(12) United States Patent
Subramanian

(10) Patent No.: US 6,252,099 B1
(45) Date of Patent: Jun. 26, 2001

(54) FLUOROCARBON MANUFACTURING PROCESS

(75) Inventor: Munirpallam A. Subramanian, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/536,349

(22) Filed: Mar. 27, 2000

Related U.S. Application Data

(62) Division of application No. 09/360,959, filed on Jul. 27, 1999, now Pat. No. 6,096,932.
(60) Provisional application No. 60/094,387, filed on Jul. 28, 1998.

(51) Int. Cl.$^7$ .............................. C07F 1/08; C01G 3/00; C07C 19/08
(52) U.S. Cl. ............................ 556/112; 423/23; 570/124
(58) Field of Search ............................. 556/112; 423/23; 570/124

(56) References Cited

U.S. PATENT DOCUMENTS

| 2,631,170 | 3/1943 | Fowler . | |
| 2,892,000 | 6/1959 | Skiles | 260/653.4 |
| 3,398,203 | 8/1968 | Olson | 260/653.3 |
| 4,394,527 | 7/1983 | Fischer et al. | 570/143 |
| 4,978,649 | 12/1990 | Surovikin et al. | 502/416 |
| 5,756,834 | 5/1998 | Pasenok et al. | 562/493 |

FOREIGN PATENT DOCUMENTS

| 52-122310 | 10/1977 | (JP) | C07C/21/18 |
| WO 97/30932 | 8/1997 | (WO) | C01B/31/28 |

OTHER PUBLICATIONS

R.G. Plevey et al., Fluorination with Complex Metal Fluorides Part. II, *Journal of Fluorine Chemistry*, 3, 259–266, 1973/74.

Chemical Abstracts, vol. 103, No. 21, 25 Nov. 1985, Abstract No. 177956, "Hexafluoroethane" (re: JP 60 109533 A(Showa Denko K.K., Japan) Jun. 15, 1985).

Guo et al. Agnew. Chem., Int. Ed. (1998),37 (5), 630–632, May 1998.*

G. Guo et al., Ein vollständig umschlossenes A cetylendiid in $Ag_2C_2 \cdot 8AgF$**, *Agnew. Chem.*, 110/5, 652–654, Mar. 2, 1998.

G. Guo et al., A Fully Encapsulated Acetylenediide in $Ag_2C_2 \cdot 8AgF$**, *Angew. Chem. Int. Ed.*, 37(5), 630–632, Mar. 16, 1998.

* cited by examiner

*Primary Examiner*—Johann Richter
*Assistant Examiner*—J. Parsa

(57) ABSTRACT

A process is disclosed for increasing the fluorine content of an olefinic compound of the formula $C_nH_mF_{2n-m}$, where n is an integer from 2 to 6 and m is an integer from 1 to 2n. The process involves (a) contacting the olefinic compound with a metal fluoride composition of the formula $(AgF)(MF_2)_x$ where M is selected from the group consisting of Mn, Fe, Co, Ni, Cu, Zn and mixtures thereof and x is a number from 0 to 1, at a temperature above 200° C. sufficient to transfer F from the metal fluoride composition to the olefinic compound, thereby producing a chemically reduced metal fluoride composition comprising metallic silver; (b) oxidizing the reduced metal fluoride composition from (a) in the presence of HF to regenerate the metal fluoride composition of the formula $((AgF)(MF_2)_x$; and (c) recycling regenerated metal fluoride composition of (b) to (a). Also disclosed are a novel composition of the formula $Ag_{10}F_8C_2$; and a process for producing hexafluoroethane which involves heating $Ag_{10}F_8C_2$ to a temperature sufficient for its decomposition.

4 Claims, No Drawings

FLUOROCARBON MANUFACTURING PROCESS

This application is a division of U.S. application Ser. No. 09/360,959, filed Jul. 27, 1999, now U.S. Pat. No. 6,096,932, and claims the priority benefit of U.S. Provisional Application No. 60/094,387, filed Jul. 28, 1998.

FIELD OF THE INVENTION

This invention relates to processes for the manufacture of fluorinated hydrocarbons, particularly the production of fluorinated olefins such as vinyl fluoride and for the manufacture of hexafluoroethane using fluoride compositions containing silver.

BACKGROUND

Vinyl fluoride (i.e., $CH_2=CHF$ or VF) is a useful monomer for the preparation of fluorocarbon polymers which have excellent weathering and chemical resistance properties.

Vinyl fluoride can be produced from acetylene and hydrogen fluoride using mercury catalysts. It can also be produced by the dehydrofluorination of 1,1-difluoroethane (i.e., $CHF_2CH_3$ or HFC-152a). U.S. Pat. No. 2,892,000 discloses a process for the manufacture of vinyl fluoride and 1,1-difluoroethane. In this process HF and acetylene are passed over a chromium catalyst (e.g., a chromium oxide or chromium salt catalyst) to obtain mixtures of VF and HFC-152a. A process is also disclosed in this patent for the conversion of product HFC-152a to VF using these catalysts.

Japanese Patent Application No. 52-122310 discloses a process for the manufacture of vinyl fluoride by the reaction of ethylene, HF and oxygen in the presence of a catalyst comprising metallic palladium, copper chloride and, optionally, a chloride of zinc, aluminum, cerium, iron, or nickel. The catalyst was pretreated with HF.

Hexafluoroethane is useful electronic gas. There is an ongoing interest in developing processes for the production of fluorinated olefins such as vinyl fluoride and for the production of hexafluoroethane, especially processes which do not involve the use of chlorine compounds.

SUMMARY OF THE INVENTION

A process is provided for increasing the fluorine content of an olefinic compound of the formula $C_nH_mF_{2n-m}$, where n is an integer from 2 to 6 and m is an integer from 1 to 2n. The process comprises (a) contacting the olefinic compound with a metal fluoride composition of the formula $(AgF)(MF_2)_x$ where M is selected from the group consisting of Mn, Fe, Co, Ni, Cu, Zn and mixtures thereof and wherein x is a number from 0 to 1, at a temperature above 200° C. sufficient to transfer F from the metal fluoride composition to the olefinic compound, thereby producing a chemically reduced metal fluoride composition comprising metallic silver; (b) oxidizing the reduced metal fluoride composition from (a) in the presence of HF to regenerate the metal fluoride composition of the formula $(AgF)(MF_2)_x$; and (c) recycling regenerated metal fluoride composition of (b) to (a).

This invention also provides a novel composition of the formula $Ag_{10}F_8C_2$; and a process for producing hexafluoroethane which comprises heating $Ag_{10}F_8C_2$ to a temperature sufficient for its decomposition.

DETAILED DESCRIPTION

One aspect of this invention involves the reaction of a metal fluoride composition of the formula $(AgF)(MF_2)_x$, where M and x are as defined above, with olefinic compounds of the formula $C_nH_mF_{2n-m}$. This reaction can be used to produce olefins with an increased fluorine content of the formula $C_nH_{m-1}F_{2n-m+y}$, where y is an integer between 1 and m and m is as defined above. In preferred embodiments, the olefinic compounds are ethylene and propylene and the reaction products comprise fluorinated olefins and fluorinated alkanes.

The $(AgF)(MF_2)_x$ functions as a regenerable fluorinating reagent (i.e., the reduced metal fluoride composition comprising silver can be oxidized back to $(AgF)(MF_2)_x$). While argentous fluoride (AgF) can be used by itself, it is preferably used as part of a mixture. The metal fluoride mixtures of this invention, $(AgF)(MF_2)_x$ where M is selected from the group consisting of Mn, Fe, Co, Ni, Cu, Zn and mixtures thereof and x is a number between 0 and 1, can be prepared by conventional engineering mixing techniques using the metal fluoride powder(s). Mixed metal compounds such as $AgMnF_3$, $AgFeF_3$, $AgCoF_3$, $AgNiF_3$, $AgCuF_3$ and $AgZnF_3$ can be prepared by heating a 1:1 molar mixture of AgF and $MF_2$, where M is as defined above, to between from about 400° C. to about 450° C. for about at least one hour in an inert atmosphere (e.g., nitrogen or argon). The powders may be made into granules or pellets.

Of note are embodiments of this reaction where vinyl fluoride is produced using ethylene as a starting material. The reaction of ethylene with the regenerable fluorinating reagent, AgF, to produce vinyl fluoride is typically accomplished in the vapor phase at a temperature of from about 250° C. to about 300° C., preferably about 300° C. The reaction of ethylene with the regenerable fluorinating reagent, $(AgF)(MF_2)_x$, to produce vinyl fluoride is done in the vapor phase at a temperature of between about 250° C. to about 500° C. The reaction pressure can be subatmospheric, atmospheric or superatmospheric; generally near atmospheric pressures are preferred.

The reaction of propylene with silver fluoride (AgF) can produce fluoroalkenes (e.g., $CH_2=CFCF_3$, $CHF=CHCF_3$ and $C_3HF_5$) and fluoroalkanes (e.g., $CH_3CHFCH_3$). Without wishing to be bound by theory, it is thought that the fluoroalkanes are a secondary product (i.e., they are formed by the addition of HF to a fluoroalkene).

The contact time is typically from about 1 to about 120 seconds (e.g., from about 5 to 60 seconds).

In an embodiment of this invention, ethylene is contacted with a metal fluoride mixture of the formula $(AgF)(MF_2)_x$. Vinyl fluoride is produced in an amount essentially equal to the stoichiometric amount of argentous fluoride, and if cupric fluoride is present (i.e., M is at least partially Cu and x is greater than 0), additional vinyl fluoride in the amount of cupric fluoride in the metal fluoride mixture can be produced. During the course of the reaction the silver fluoride is reduced to silver metal and the cupric fluoride, if present, to copper metal. This reaction is believed to proceed as shown in equations 1 and 1a.

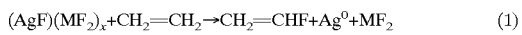
$$(AgF)(MF_2)_x + CH_2=CH_2 \rightarrow CH_2=CHF + Ag^0 + MF_2 \quad (1)$$

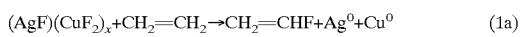
$$(AgF)(CuF_2)_x + CH_2=CH_2 \rightarrow CH_2=CHF + Ag^0 + Cu^0 \quad (1a)$$

When argentous fluoride is used by itself to fluorinate ethylene at 300° C., the silver fluoride is converted to a new composition of matter, $Ag_{10}F_8C_2$. Of note is a composition of that formula having a tetragonal structure. Less vinyl fluoride is produced than when the mixed fluoride reagent is used since most of the fluorine is consumed in producing the new silver composition. This is shown schematically in equation 2.

$$AgF + CH_2=CH_2 \rightarrow CH_2=CHF + Ag^0 \text{ (metal)} + Ag_{10}F_8C_2 \quad (2)$$

If the ($Ag^0$ (metal)+$Ag_{10}F_8C_2$) mixture is reacted with additional ethylene at a temperature of at least 350° C., then no vinyl fluoride is produced. Instead, the following products are formed; 1,1-difluoroethylene ($CH_2=CF_2$) a fluoromonomer, pentafluoroethane ($CHF_2CF_3$) a refrigerant, 1,1,1-trifluoroethane ($CH_3CF_3$) a refrigerant and hexafluoroethane ($CF_3CF_3$) a plasma etchant. It is believed that most of the silver is in the metallic state after this reaction.

If $Ag_{10}F_8C_2$ is isolated and heated at about 350° C. in an inert atmosphere such as nitrogen, then the major fluorinated hydrocarbon product is hexafluoroethane, as shown in equation 3.

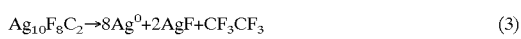

$$Ag_{10}F_8C_2 \rightarrow 8Ag^0 + 2AgF + CF_3CF_3 \quad (3)$$

Hexafluoroethane is useful as a plasma etchant in semiconductor device fabrication.

Argentous fluoride can be regenerated from the fluoride-depleted reagent either by reacting with oxygen and HF at a temperature between about 250° C. to about 500° C. or by converting the fluoride-depleted reagent to a stable salt (e.g, $AgNO_3$ or $Cu(NO_3)_2$) and reacting said salt with HF. The oxygen may be diluted with inert gases such nitrogen and argon.

The present invention process may be done in a single step by co-feeding HF, the alkene and an oxidizing agent such as oxygen and hydrogen peroxide. In this embodiment the fluoride depleted reagent is continuously regenerated.

Also of note are processes which use of pairs of reaction zones, each containing a metal fluoride composition. In this embodiment, olefinic starting material is fed to one of the reaction zones while metal fluoride regeneration is accomplished in the other zone.

Without further elaboration, it is believed that one skilled in the art can, using the description herein, utilize the present invention to its fullest extent. The following embodiments are to be construed as illustrative, and not as constraining the remainder of the disclosure in any way whatsoever.

Examples

Legend
FC-116 is $CF_3CF_3$
FC-143a is $CH_3CF_3$
FC-1141 is $CH_2=CHF$
FC-125 is $CHF_2CF_3$
FC-1132a is $CH_2=CF_2$ General Procedure A Hastelloy® nickel alloy tube (⅜" (9.5 mm) o.d.×3" (76.2 mm) long) was packed with a fluorinating reagent. The fluorinating reagent was heated to reaction temperature under a nitrogen flow. Ethylene was then passed over the fluorinating reagent at a 30 cc/min. flowrate. During the reaction period, the reactor bed temperature was monitored by an internal thermocouple, located immediately upstream of the reactor bed. Reaction products were analyzed using a Hewlett Packard 6890 Gas Chromatograph/5973Mass Spectrometer. All analyses are reported in area %.

Example 1

Preparation of Vinyl Fluoride (AgF)

The above General Procedure was followed using ethylene and argentous fluoride (AgF, 6 g) powder (100–250μ) as the fluorinating reagent. Results at 300° C. and 350° C. are shown in Table 1.

TABLE 1

| T(° C.) | % FC-1141 | % FC-1132a | % FC-125 | % FC-143a |
|---|---|---|---|---|
| 300 | 3.1 | — | — | — |
| 300 | — | — | — | — |
| 350 | — | 4.3 | 0.2 | 0.3 |

Examples 2–8

Preparation of Vinyl Fluoride ($CuF_2$/AgF)

The above General Procedure was followed using ethylene and various molar ratios of $CuF_2$/AgF as the renerable reagent. The fluorinating reagent was prepared by mixing the components in an agate mortar and pestle in a drybox. The mixture was then heated in nitrogen in the Hastelloy® nickel alloy tube reactor described above at 400° C. for about 6 to 12 hours followed by cooling to reaction temperature. At this point ethylene was passed over the fluorinating reagent. Results at various temperatures are shown in Table 2.

TABLE 2

| Ex. No. | $CuF_2$:AgF molar ratio | Cat. Wt. (g) | T ° C | Area % FC-1141 |
|---|---|---|---|---|
| 2 | 1:1 | 3 | 350 | 5.2 |
| 3 | 1:1 | 3 | 375 | 8.2 |
| 4 | 1:3 | 3 | 360 | 10.8 |
| 5 | 1:3 | 5 | 350 | 8.2 |
| 6 | 1:9 | 5 | 300 | 6.0 |
| 7 | 1:19 | 6 | 300 | 3.9 |
| 8 | 1:49 | 6 | 300 | 4.2 |

Examples 9–13

Preparation of Vinyl Fluoride ($AgMF_3$)

The above General Procedure was followed using ethylene and $AgMF_3$, where M is selected from Co, Mn, Ni, Zn and Cu, as the renerable reagent. The fluorinating reagent was prepared by grinding the fluorinating reagent components AgF and $MF_2$ in an agate mortar and pestle in a drybox. The mixture was then heated in nitrogen at 400° C. to 450° C. for about 12 hours followed by cooling to reaction temperature. X-ray diffraction showed the formation of $AgMF_3$ phases. At this point ethylene was passed over the fluorinating reagent. Results at various temperatures are shown in Table 3.

TABLE 3

| Ex. No. | $AgMF_3$ M | Cat. Wt. (g) | T | Area % FC-1141 |
|---|---|---|---|---|
| 9 | Co | 4.2 | 350 | 0 |
|  |  |  | 400 | 7.7 |
|  |  |  | 450 | 0 |
|  |  |  | 500 | 0 |
| 10 | Mn | 4.2 | 350 | 0 |
|  |  |  | 400 | 1 |
|  |  |  | 450 | 5.8 |
|  |  |  | 500 | 0 |
| 11 | Ni | 3.5 | 350 | 4.6 |
|  |  |  | 400 | 5.6 |

TABLE 3-continued

| Ex. No. | AgMF$_3$ M | Cat. Wt. (g) | T | Area % FC-1141 |
|---|---|---|---|---|
|  |  |  | 450 | 5.6 |
|  |  |  | 500 | 0 |
| 12 | Zn | 3.6 | 350 | 0 |
|  |  |  | 400 | 3.2 |
|  |  |  | 450 | 3.9 |
|  |  |  | 500 | 4.2 |
| 13 | Cu | 5.0 | 350 | 9.4 |
|  |  |  | 400 | 13.4 |
|  |  |  | 450 | 25.5[a] |
|  |  |  | 500 | 16.4 |

[a]1% $C_2H_5F$ was also identified in the product

The end product of the fouorination reagents were identified as Ag+CoF$_2$, Ag+MnF/$_2$, Ag+NiF$_2$, Ag+ZnF$_2$ and Ag+Cu for Examples 9 to 13 respectively.

Example 14

Reaction of Proplene

The above General Procedure was followed using propylene and argentous fluoride (AgF, 5 g) power (100–250μ) as the fluorinating reagent. At 350° C. the product were (area %) 5% $CH_2$=$CFCF_3$, 5% $CHF$=$CHCF_3$, 4% $C_3HF_5$ and 9% $CH_3CHFCH_3$.

Example 15

$Ag_{10}F_8C_2$ Preparation

The above General Procedure was followed using AgF as a fluorinating reagent. Ethylene was passed over the fluorinating reagent at 300° C. until no more vinyl fluoride was observed. As the level of vinyl fluoride decreases to a nearly non-detectable level in the mass spectreometer spectre, the sample was then quenched with high nitrogen flow (apprx. 200 cc/min conjunction with opening the furnace door for fast cooling. X-ray difraction data showed the formation of Ag metal along with a phase with a formula $Ag_{10}F_8C_2$. The phase has a tetragonal structure with a =7.476 Å and b=10.348 Å (space group P 4/n).

Further heating of $Ag_{10}F_8C_2$ in ethylene at 350° C. gave FC-1132a, FC-125,FC-143a and FC-116 (see Table 15).

$Ag_{10}F_8C_2$ (1.72 g) was heated to 300° C. under nitrogen. The reactor temperature was then raised while the reaction gases were monitored with the GC/MS. The main product was FC 116.

TABLE 15

| % FC-1132a | % FC-125 | % FC-116 | % FC-143a |
|---|---|---|---|
| 1.1 | 3.3 | 2.9 | Trace |

What is claimed is:
1. A compound having the formula $Ag_{10}F_8C_2$.
2. A composed of claim 1 having a tetragonal structure.
3. A process for producing $CF_3CF_3$, comprising:

heating $Ag_{10}F_8C_2$ to a temperature sufficient for its decomposition.
4. A composition comprising the compound of claim 1 and metallic silver.

* * * * *